United States Patent

Mirabella

Best Available Copy

[11] 4,296,329
[45] Oct. 20, 1981

[54] ALIGNMENT DEVICE FOR COMPUTERIZED TOMOGRAPHY PHANTOMS

[75] Inventor: Paul J. Mirabella, Waukesha, Wis.

[73] Assignee: General Electric Company, Schenectady, N.Y.

[21] Appl. No.: 87,595

[22] Filed: Oct. 22, 1979

[51] Int. Cl.³ .......................................... G01N 21/00
[52] U.S. Cl. .................................. 250/491; 250/252; 250/445 T
[58] Field of Search .................. 250/252, 445 T, 491; 356/138, 150, 153, 390

[56] References Cited

U.S. PATENT DOCUMENTS

| | | | |
|---|---|---|---|
| 4,112,303 | 9/1978 | Brandt | 250/490 |
| 4,117,337 | 9/1978 | Staats | 250/491 X |
| 4,161,655 | 7/1979 | Cotic et al. | 250/385 |
| 4,223,227 | 9/1980 | Horwitz | 250/491 |

Primary Examiner—Davis L. Willis
Attorney, Agent, or Firm—Wheeler, House, Fuller & Hohenfeldt

[57] ABSTRACT

In a computed tomography system a cylindrical calibration phantom having a vertical and a horizontal crosshair on its front face is adjusted until the intersection point of the crosshairs is coincident with the isocenter of the x-ray scanner as demonstrated by the display of a reconstructed tomographic of the phantom. Vertical and horizontal intersecting coherent light beams from a laser source are then projected onto the phantom and the source is adjusted until the light beams, crosshairs and their intersections coincide. Any phantom used for any subsequent calibration only needs to be adjusted until the permanently set laser light beams coincide with its crosshairs in which case the isocenter is determined exactly again and the apparatus is ready immediately for a calibration run.

2 Claims, 5 Drawing Figures

ALIGNMENT DEVICE FOR COMPUTERIZED TOMOGRAPHY PHANTOMS

This invention relates to computed tomography and, particularly, to a method and device for aligning phantoms which are used for calibrating such apparatus.

As is well-known, computed tomography (CT) apparatus is used for obtaining x-ray attenuation data from a thin body layer for the purpose of enabling reconstruction of an x-ray image that allows the layer to be viewed in an axial perspective. Computed tomography apparatus comprises an x-ray tube located on one side of a human body undergoing an x-ray scan and a multiple element x-ray detector located on the other side of the body. The x-ray tube and detector are on a common mounting which is driven rotationally about a horizontal longitudinal axis so the tube and detector orbit the patient jointly. The x-ray beam emanating from the focal spot of the x-ray tube is collimated into a thin diverging or fan-shaped beam whose thickness corresponds with the thickness of the layer in the body being scanned. The common mounting for the x-ray tube and multiple element detector is part of a gantry which permits the mounting and, hence, the rotational plane of the tube and detector to be tilted about a laterally extending horizontal axis to which the longitudinal axis is perpendicular. This permits making a scan and obtaining x-ray attenuation data for an image of a transverse slice or layer of the body which is at an angle relative to vertical and to the longitudinal axis. It is necessary for the gantry to be constructed so the intersection point of the longitudinal and transverse axes does not shift in any direction when the rotational plane is tilted. The intersection point is called the isocenter. The longitudinal axis projects through the isocenter.

Typically, the x-ray source is pulsed on and off at a rapid repetition rate during a rotational scan. Every time the source is on, an x-ray view is taken and the array of detector elements which intercept the diverged x-ray beam after it has emerged from the body produce analog signals that are representative of x-ray attenuation by the sum of small volume elements of the body through which the rays in the beam pass to the respective elements in the detector. As is well-known, the analog signals obtained during each x-ray view are converted to digital data which is normalized and used by a computer, executing an image reconstruction algorithm, to produce a CT number matrix or pixel data which is used by a display controller to effect display of the reconstructed image on the cathode ray tube of a video monitor.

It is necessary to calibrate CT apparatus periodically. Calibration requires scanning a phantom and displaying its image. The phantom is mounted on the table which is used to advance a patient into the scanning beam during regular examinations. Typical phantoms comprise a plastic cylinder filled with water or they can be solid plastic cylinders having an axial thickness at least as great as the thickness of the fan-shaped x-ray beam and they may have various diameters so that one may be chosen that fits within the circular image reconstruction zone of the CT apparatus. Phantoms have fixed x-ray attenuation properties corresponding with some tissue such as muscle tissue in the body. Scanning the phantom enables the computer to generate CT numbers or attenuation data corresponding with various areas in the reconstruction zone. The data readout and processing system electronics may drift somewhat in a day or two. So when the phantom attenuation data is in the processing system the electronics are adjusted until the CT numbers correspond with those expected of the phantom. This amounts to establishing a reference level to which all data taken with a patient can be referred and normalized. If the system were not calibrated in this fashion there would be no way of knowing whether density differences in picture elements of the displayed reconstructed images were due to differential attenuation by body tissue or to electronic drift and other errors.

Before the phantom scan for calibration purposes is made the computer must have data for it to determine where the center of rotation, that is, the longitudinal axis or isocenter is located. For this purpose, the flat circular rear face of each phantom customarily has cross hairs scribed or printed on it. The object of a set up in preparation for calibration is to shift the phantom around until the intersection point of the phantom cross hairs is aligned with the isocenter.

Before the new phantom alignment method and device described herein was developed, alignment was obtained by an iterative method. A technician would look at the cross hairs from behind the CT apparatus and make a judgment as to the location of the cross hair intersection relative to the isocenter or center of the reconstruction circle. Then the technician would use the bilaterally adjustable phantom mounting device to position the cross hair intersection to where it seemed to be coincident with the isocenter.

When a first approximation was made, the phantom was subjected to an x-ray scan as described above and after the computer had developed the image reconstruction data, the image was displayed on the monitor. If the phantom was not properly aligned, one side of the displayed image might be cut off or distorted in which case the phantom was shifted and the process repeated again and again until the computer indicated that the isocenter had been found. A computer program has been used which informed the technician which way to shift the phantom to get it to appear as a full circle on the display screen. This iterative method of calibration wasted a lot of technician's time and reduced output of the costly apparatus since determination of the isocenter location and recalibration is done at least once per day in some clinics and more or less in others.

SUMMARY OF THE INVENTION

An object of the present invention is to provide a method and device for establishing the center of a phantom coincident with the isocenter of the CT gantry quickly, accurately and reproducibly.

A further object is to provide an isocenter locating device which requires that the iterative process be carried out only once during an initial set-up so that at any subsequent time when a phantom is installed for calibration purposes its center can be quickly adjusted into coincidence with the isocenter without requiring that a succession of test images be reconstructed and displayed.

Still another object is to provide a method and device for aligning the center of a phantom with the isocenter on the first try with an accuracy to within 0.5 mm.

Briefly stated, the new alignment system employs a laser light source and a phantom having cross hairs marked on its face. The laser light source is mounted on a permanent building part such as a wall intersected by the longitudinal or rotational axis of the scanner and behind the gantry in which the scanner is mounted. The laser light source is in a box in which there are short and narrow horizontal and vertical slits for emergence of sharply focused horizontally and vertically extending orthogonally related laser light beams. Because the light from the laser source is coherent, there is no substantial divergence or fanning out of the vertical and horizontal bands of light which emerge from the orthogonally arranged slits. Thus, very fine luminous crossed lines are projected onto the phantom. The light lines are very visible and not affected by parallax so it is easy to adjust the phantom until the intersection of the crossed lines of light coincides with the intersection of the cross hairs on the phantom. When the isocenter is found for one phantom in accordance with the procedure described earlier, the laser source is adjusted so that the crossed lines of laser light coincide with the cross hairs on the phantom face. Then all subsequent phantoms need only be adjusted up and down and sideways until the crossed laser light lines coincide with the phantom cross hairs so the isocenter is, in effect, permanently determinable.

Use of a laser light source in connection with computerized tomography apparatus is not new per se as such sources have been used to project beams of light on a patient to aid in coordinating a zone on a patient's anatomy with an x-ray beam scan path. Such use is shown in U.S. Pat. No. 4,117,337.

How the above-mentioned objects and other more specific objects of the invention are achieved will be evident in the more detailed description of a preferred embodiment of the invention which will now be set forth in reference to the drawing.

DESCRIPTION OF THE DRAWING

FIG. 3 is a diagram for facilitating explanation of the invention;

FIG. 4 is a front elevation view of a computed tomography calibration phantom; and FIG. 5 is a diagram of a mechanism for holding a phantom during an isocenter location test.

DESCRIPTION OF A PREFERRED EMBODIMENT

Figure 1:
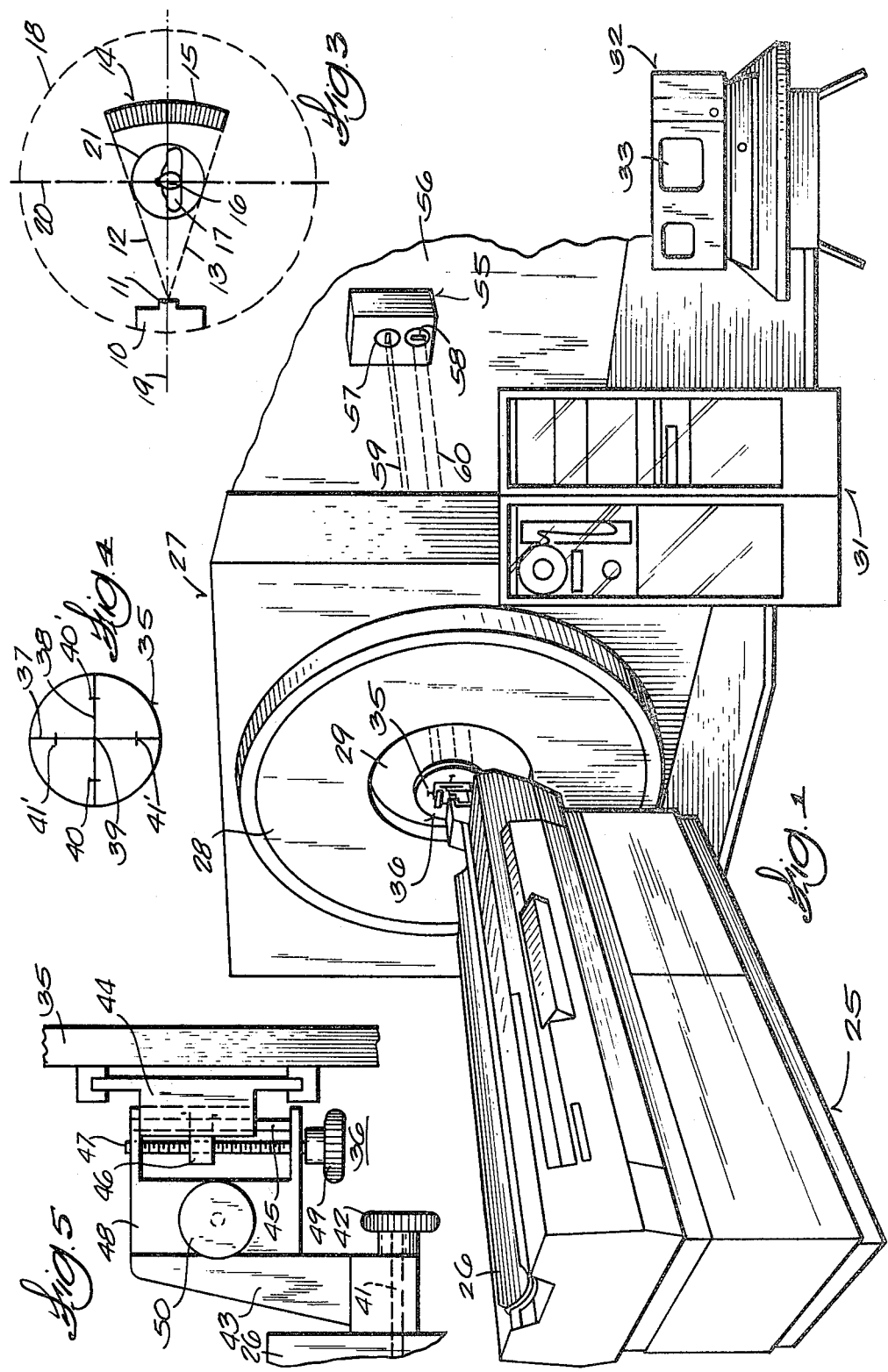
FIG. 1 is a perspective view of a computed tomography system presently set up for locating the isocenter.

The components of a computed x-ray tomography scanner (CT scanner) with which the new phantom alignment device may be used are illustrated in FIG. 3. The scanner comprises a source of penetrating radiation such as x-radiation or gamma radiation. For the sake of brevity, the terms x-ray and x-radiation are to be construed herein as embracing gamma rays and gamma radiation sources. X-ray source 10 is associated with a collimator 11 which collimates the x-rays emerging from a source, such as the focal spot of an x-ray tube, into a thin fan-shaped beam whose boundary rays are indicated by the dashed lines 12 and 13. Ordinarily, the diverging or fan-shaped beam is about 1 cm. thick. The beam is projected toward an x-ray detector 14 which is comprised of an array of adjacent and arcuately arranged detector cells 15. A suitable detector is shown in U.S. Pat. No. 4,161,655. X-ray source 12 and detector 14 are on a common mounting, not shown, which is rotatable about a longitudinally extending axis 16. In FIG. 3, the longitudinal direction is perpendicular to the plane of the drawing. The body 17 of a patient who is to undergo an x-ray scan is disposed in a recumbent position between the x-ray source and detector and the longitudinal axis 16 extends longitudinally through the body. The orbital path of the x-ray source 10 is indicated by the dashed circular line marked 18 and, of course, detector 14 follows a concentric path during an orbital scan. The circular zone to which the boundary rays 12 and 13 are tangent is marked 21. This circular zone is called the image reconstruction zone as nothing outside of it will appear in the displayed image.

In the scanning process, source 10 and detector 14 are orbited through 360° during which time the x-ray source is pulsed on and off repetitively and analog signals corresponding with x-ray attenuation along the multiple ray paths through the body are produced. As indicated earlier, the signals are processed in a manner that ultimately results in a CT number data matrix corresponding with the picture elements of the reconstructed image. The CT number matrix is used by a display controller to control display of the image.

In FIG. 3, the plane in which the x-ray source 10 and detector 14 orbit jointly is vertical and the longitudinal axis 16 is perpendicular to this vertical plane. However, some diagnostic procedures require a view of a body layer which is angulated relative to vertical in which case the orbital plane it tilted away from vertical on a horizontal axis which, in FIG. 3, is marked 19. A vertical plane or line extending through longitudinal axis 16 is marked 20. Longitudinal axis 16, horizontal tilting axis 19 and vertical 20 are orthogonal to each other and intersect at a common point which is known as the isocenter of the system.

The computer algorithm requires data indicative of the location of the isocenter to use as a reference point for reconstructing x-ray images wherein the displayed picture elements correspond with the location of the volume elements in the body layer being imaged. As stated earlier, a phantom is used for determining the isocenter and for calibrating the CT system.

Figure 2:
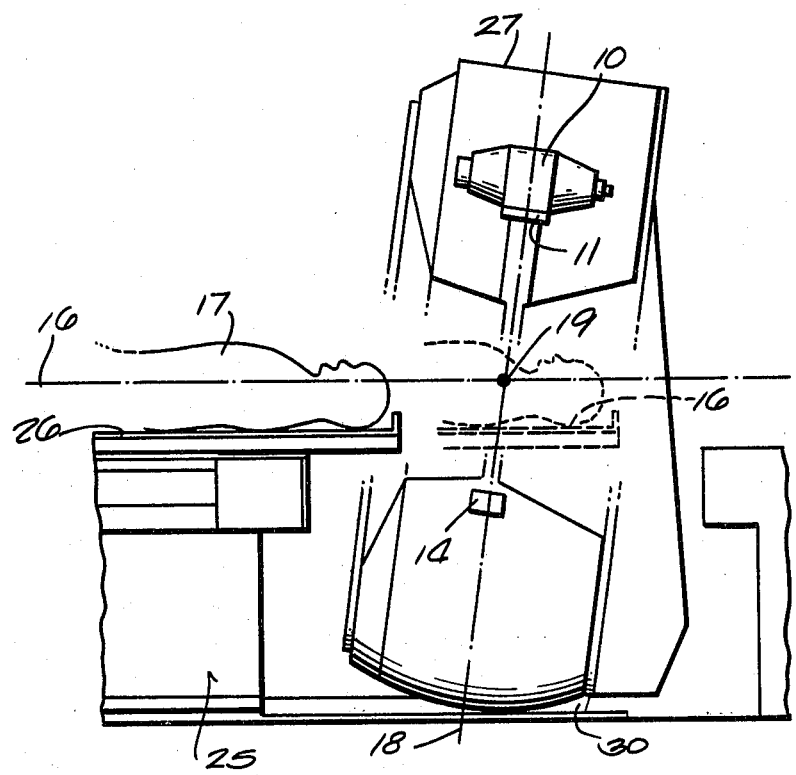
FIG. 2 is a right side partial sectional view of a computed tomography system showing the gantry in a tilted position.

Typical computed tomography apparatus is shown in FIGS. 1 and 2 and will be described only in such detail as is necessary to demonstrate the construction and function of the new phantom alignment device and method.

In FIG. 1, a patient supporting table is designated generally by the reference numeral 25. Table 25 has an x-ray transmissive top 26 on which a body, such as the body 16 in FIG. 2, may be supported in a recumbent position. Table top 26 in FIG. 1 is adapted for being translated longitudinally so that it extends in cantilever fashion from table body 25 for the purpose of disposing the body in a position for being scanned with the fan-shaped x-ray beam. Scanning is performed with a gantry whose housing is marked 27 in FIG. 1 and which is shown in section in FIG. 2. In FIG. 1, housing 27 has a circular shroud 28 which defines a central circular opening 29. Image reconstruction circle 21 is ordinarily concentric with opening 29. The body is indexed through this opening in steps to obtain scans of successive longitudinally adjacent body layers while the body is supported in cantilever fashion on table top 26. FIG. 2 depicts the body 17 in dashed lines where it is advanced for being penetrated by the fan-shaped beam in connection with making a scan of a body layer.

In FIG. 2, the x-ray source is marked 10, the x-ray beam collimator is marked 11 and the detector is marked 14 as they are in FIG. 3. The longitudinal axis 16 of the system about which the x-ray source and detector orbit is shown as extending through the patient 17. In FIG. 2, the gantry is tilted rearwardly or cranially about central transverse axis 19 which is normal to the plane of the drawing, thus appearing as a point, and is perpendicular to longitudinal axis 16. For the sake of example, the orbital plane for the x-ray source 10 and detector 14 is shown tilted in FIG. 2 as would be the case if an axial view of an angulated layer of the body was desired. The gantry is constructed such that the point of intersection of the various axes of the system does shift when the gantry is tilted. The gantry has a base 30 about which its components can be tilted and rotated about central longitudinal axis 24. A suitable gantry mechanism is described in greater detail in U.S. Pat. No. 4,112,303.

Referring back to FIG. 1, the computer which is used for image reconstruction and various other purposes, is represented schematically and identified generally by the reference numeral 31. The system control and display console is indicated generally by the reference numeral 32. It has a cathode ray tube on whose screen 33 reconstructed images of body layers or of a phantom undergoing scanning are displayed.

In FIG. 1, the apparatus is set up for undertaking calibration using a phantom. The phantom consists of a cylinder 35 mounted on an adjustable holder which is generally designated by the reference numeral 36. Cylinder 35 may be made of solid plastic such as methyl methylcrylate, one brand of which is known by the trademark Lucite. In the alternative, the phantom may be made of a low x-ray absorbing hollow plastic cylinder whose ends are closed with disks of similar material and whose interior volume is occupied by water. By way of example, the cylinder may be about two inches thick in the axial direction and have a diameter of about 16 inches although larger and smaller diameter cylinders are used for some calibration procedures. Holder 36 secures the phantom on the end of longitudinally translatable table top 26 temporarily during the alignment operation and, of course, the phantom and holder are removed during normal operation of the apparatus.

An end face of the phantom cylinder 35 is shown in FIG. 4. It has a fine vertical line 37 and a fine horizontal line 38 inscribed or printed on it. Lines 37 and 38 are equivalent to cross hairs and they intersect at right angles at a center point marked 39. There are tick marks such as 40 and 41 on the horizontal and vertical cross hairs, respectively.

The phantom holder with phantom 35 attached is shown in FIG. 5. The phantom holder is adapted for being fastened to the end of table top 26 with a screw 41 that is turnable with a knob 42 to clamp the phantom holder base 43 to the table top. The phantom holder is designed for shifting the phantom 35 up and down or sideways to establish the intersection point 39 of its cross hairs 37 and 38 coincident with longitudinal axis 16 which is the center of rotation of the scanner. In the FIG. 5 example, holder 36 is provided with a carriage 44 which slides on bars 45 and has an internally threaded nut 46 projecting integrally from it. A lead screw 47, journaled in frame 48 at its opposite ends, extends through internally threaded nut 46 and can be turned to raise and lower the carriage. This, of course, raises or lowers the phantom 35 which is hung on carriage 44. The lead screw 47 is turned with a knob 49. Another knob 50 may be turned to cause the carriage to shift transversely although the details of the carriage with which it cooperates are not shown since a reasonably skilled mechanic can devise a support for shifting the phantom in any desired direction.

A unique feature of the present disclosure is to use a source of coherent light such as a laser light source for finding the isocenter of any phantom that is mounted on the table top in connection with the isocenter location procedure. The laser source is in a box 55 mounted on a wall 56 of the room in which the computed tomography equipment is located as is evident from inspection of FIG. 1. The laser beam source comprises a class II helium-neon gas laser having a beam splitter and lenses which project a luminous cross hair pattern on the face of phantom 35 which is visible in FIG. 4. The internal components of laser source 55 are not shown and are not, by themselves, considered to be part of the invention. A suitable laser source is available from Gammex, Inc. in Milwaukee, WI. The laser source box 55 has a horizontal slit 57 and a vertical slit 58 through which thin horizontally and vertically oriented beams 59 and 60 emerge respectively. Thin vertical beam 60 is aimed toward phantom disk 35 for falling in coincidence with vertical cross hair 37 on the phantom as depicted in FIG. 4. Thin horizontal beam 59 is aimed for falling in coincidence with horizontal cross hair 38 of the phantom. The crossed perpendicular light beams 59 and 60 are very sharp or thin and can be seen easily on the surface of phantom disk 35 by an observer standing behind gantry 27 or next to the laser light source 55 as shown in FIG. 1. Only one laser, not shown, is present in box 55. Its sharp thin output beam is projected to an adjustable reflector system, not shown, which delivers the separate horizontal and vertical beam. Because the beams are of coherent light, they remain thin and sharp even when they are projected onto a phantom which is a great distance from the source. In an actual embodiment, the widths of the horizontal and vertical light lines on the phantom face are slightly under 3 mm. when the laser source is about three meters from the phantom.

This degree of luminous line sharpness was found to be unattainable in a test arrangement which employed an incoherent light source such as an incandescent lamp even when a sophisticated optical focusing system was used. Incidentally, the tick marks 40 and 41 are not absolutely necessary. They just provide a rough visible check as to where the edges of the cross beams are. The ultimate adjustment is to have the orthogonally related laser light beams coincident with the phantom cross hairs and with the intersection point of the beams coincident with the intersection point 39 of the cross hairs.

The laser alignment system is used in the following manner. For an initial set up or calibration of the tomography apparatus, a phantom disk 35 of a size corresponding with the desired reconstruction circle size is held on holder 36 in alignment with the laser source. A tomographic scan of the phantom is then made by employing the x-ray source 10 and detector 14 components of the scanner as described above. The reconstructed image of the phantom is displayed on cathode ray tube screen 33 in the control and display console 32. On the first try, it is likely that the displayed image will be distorted or cut off at its margins since it is unlikely that the computer will be provided with data indicative of the exact location of the isocenter at this time. As stated previously, however, the computer is provided with software that indicates to the operator which direction or directions the phantom should be shifted for the image to be constructed in proper reference to the isocenter. This iterative process is carried on until the isocenter is located and the image of the phantom is properly reconstructed and displayed. Then the laser source is adjusted so that horizontal beam 59 from the source lands exactly coincident with horizontal cross hair 38 on the phantom and vertical beam 60 lands exactly coincident with vertical cross hair 37 on the phantom which means that the intersection line or point of the crossed beams will coincide with the intersection point 39 of cross hairs 37 and 38. The individual laser beams 59 and 60 then remain permanently in whatever orientation they are adjusted at the end of the first alignment procedure. After a single scan for calibration purposes is made, phantom 35 and its holder 36 may then be removed from the table since the system is ready for scanning patients.

Subsequently, that is, at any time that the tomography apparatus is to be recalibrated using a phantom, whatever phantom is to be used will again be supported on holder 36 in the path of the light beams from the laser source 55. When the laser source is turned on the operator may observe that the crossed laser light beams 59 and 60 do not fall in coincidence with vertical cross hairs 37 and 38. This means that the phantom center point 39 does not coincide with the longitudinal axis nor the isocenter of the system. All that is necessary to do under these circumstances is to turn lead screw knobs 49 and 50 of phantom holder 36 until the thin horizontal light beam 59 coincides with horizontal cross hair 38 and the vertical light beam 60 coincides with vertical cross hair 37 of the phantom. The intersection of the light beams will then be coincident with center point 39 of the phantom cross hairs which is on the isocenter of the system. Thus, the center of the cylindrical phantom will be coincident with the isocenter and the cylinder will be concentric with the reconstruction circle. There is no need for any feedback of adjustment direction information under the control of the computer hardware at this time because when the light beams and cross hairs are adjusted to coincidence, it is positively known that computer will be provided with exact information as to the location of the isocenter. A scan of the phantom is them made for calibration purposes and, at the same time, the displayed image may be observed to simply verify that the image is concentric with the isocenter.

In practice, the data which is indicative of the isocenter and which is provided to the computer at the time the first phantom is properly located is stored on magnetic disk so it is available when any phantom is installed for future calibration runs. Disk storage permits the apparatus to be completely deenergized without loss of the isocenter identifying data.

I claim:

1. Improved means for aligning the center of a calibration phantom with the isocenter of a computed tomography scanner apparatus, said scanner including an x-ray detector and an x-ray source for projecting an x-ray beam toward said detector while said source and detector are being orbited jointly about a longitudinal axis extending through said isocenter and constituting the center of an image reconstruction circle which lies between said source and detector in the x-ray beam path, said phantom comprising an x-ray transmissive cylinder having an end surface on which there are visible cross hairs which have a point of intersection coincident with the denter of the cylinder and which point it is desired to establish coincident with the isocenter for calibrating the scanner apparatus, and means for supporting said phantom is said beam path and for being shifted in any direction required to get said cross hair intersection and said longitudinal axis to coincide, said improved aligning means comprising:

a laser light source means for being fixed in a predetermined location remotely from said phantom and generally in the direction in which said longitudinal axis extends, said laser light source being operative to project thin intersecting beams of coherent light which have the same angles between them as said cross hairs onto said phantom surface as luminous lines with the point of intersection of said beams being coincident with said isocenter and with the beams being simultaneously coincident with said cross hairs, said laser light source being adjustable to cause said beams to be coincident with the cross hairs of one of said phantoms after said one phantom has been shifted by means of its supporting means to a position where said center of the phantom cylinder coincides with said isocenter such that when any similar phantom is mounted for calibration purposes it will only be necessary to shift it until said intersecting laser light beams are coincident with its cross hairs to establish the similar phantom on the isocenter.

2. A method of locating phantoms properly for calibrating computed tomography apparatus at different times, comprising:

positioning a cylindrical phantom which has cross hairs on an end face with the intersection point of the cross hairs approximately coincident with the isocenter of a computed tomography x-ray beam scanner that includes an x-ray source and detector which are movable together to effect a scan of the phantom, scanning said phantom to obtain signals from said detector representative of x-ray attenuation by said phantom at various angles about said isocenter, processing said signals by means including a computer to develop data for enabling reconstructing circular image of said phantom, displaying a reconstructed image of said phantom and ascertaining if any part of the margin of said image is cut off or not uniformly concentric with said isocenter, shifting said phantom and repeating said scanning and displaying as required until complete circularity and concentricity is obtained, adjusting a laser light source until the intersecting vertically and horizontally extending beams of coherent light which it projects are coincident with said cross hairs on the phantom and then fixing the adjustment of the laser nominally permanently, then on subsequent occasions when any comparable phantom is to be scanned for calibration purposes, activating said laser light source for it to project its intersecting beams on said phantom, and shifting said comparable phantom until its cross hairs and said beams are coincident whereupon said cylindrical phantom will be exactly concentric with said isocenter.

* * * * *